United States Patent [19]

Funk

[11] Patent Number: 5,104,419
[45] Date of Patent: Apr. 14, 1992

[54] SOLID WASTE REFINING AND CONVERSION TO METHANOL

[76] Inventor: Harald F. Funk, 68 Elm St., Murray Hill, N.J. 07974

[21] Appl. No.: 486,394

[22] Filed: Feb. 28, 1990

[51] Int. Cl.$^5$ .......................... C10J 3/14; C10J 3/60; C10J 3/66
[52] U.S. Cl. .................. 48/209; 48/197 R; 252/373; 518/703
[58] Field of Search .......... 48/209, 197 R, 203; 201/36, 29, 2.5, 25, 37, 30; 518/703; 62/12; 252/373

[56] References Cited

U.S. PATENT DOCUMENTS

| | | |
|---|---|---|
| 3,849,332 | 11/1974 | Bailey et al. |
| 3,864,097 | 2/1975 | Urban |
| 3,928,000 | 12/1975 | Child et al. |
| 3,970,524 | 7/1976 | Funk ........................ 201/2.5 |
| 4,031,189 | 6/1977 | Gemmeke et al. |
| 4,078,973 | 3/1978 | Choi et al. |
| 4,082,615 | 4/1978 | Komuro et al. |
| 4,101,412 | 7/1978 | Choi |
| 4,162,959 | 7/1979 | Duraiswamy |
| 4,301,147 | 11/1981 | Williams et al. |
| 4,348,487 | 9/1982 | Goldstein et al. ............ 48/197 R |
| 4,353,713 | 10/1982 | Cheng |
| 4,406,118 | 9/1983 | Funk |

FOREIGN PATENT DOCUMENTS

2460901 7/1975 Fed. Rep. of Germany ...... 518/703

Primary Examiner—Joye L. Woodard
Attorney, Agent, or Firm—Sixbey, Friedman, Leedom & Ferguson

[57] ABSTRACT

A process for converting solid waste into a synthesis suitable for producing liquid fuel, comprising (a) partially oxidizing and combusting solid waste material in a closed combustion zone at a temperature of 800°–1000° C. and at a pressure below ambient to produce combustion gases by introducing into the combustion zone a gaseous oxidant comprising oxygen having a purity of at least 95% by volume and carbon dioxide in an oxygen to carbon dioxide ratio, by volume, of about 50:50, (b) conducting the combustion gases, oxygen and carbon dioxide through the solid waste material; (c) withdrawing a producer gas comprising the combustion gases and any unreacted oxygen and carbon dioxide; (d) removing particulate matter from the producer gas; (e) separating carbon dioxide from the producer gas and recycling a portion of the separated carbon dioxide to the combustion zone; (f) separating the less volatile, condensable components of the carbon dioxide-free producer gas, from the more volatile, non-condensable synthesis gas components thereof, and (g) compressing the producer gas at some time prior to the completion step (e). In a preferred embodiment, the more volatile components and at least a portion of the separated carbon dioxide from step (e) are admixed and the resulting admixed gas mixture is reacted to form methanol. Preferably, the less volatile components are converted by chemical reaction to hydrogen and the hydrogen is recycled into admixture with the producer gas at some time prior to the commencement of step (e).

38 Claims, 4 Drawing Sheets

SOLID WASTE REFINING AND CONVERSION TO METHANOL

BACKGROUND OF THE INVENTION

1. Field of the Invention

The present invention relates generally to a method of beneficially utilizing solid waste materials and, more particularly, to a method for refining and converting solid waste to liquid fuel, such as methanol.

2. Description of the Prior Art

The problem of disposing of solid waste has been increasing for many years with the growth of population and is now critical in the larger cities. The usual manner of disposing of solid waste has been to use it for land fill, to dump it into water, or it incinerate it. Suitable land fill areas are becoming increasingly hard to find. Dumping solid wastes into water presents pollution problems. Incinerating solid wastes pollutes the air with harmful gases and increases its $CO_2$ content When rains remove excess $CO_2$ content from the air, the acidity of rain water is increased and this may have harmful effects on plants, animal life and buildings. Moreover, incinerators require tall stacks and scrubbers to remove harmful components from the gas and these structures are quite expensive.

Numerous efforts have been made to solve solid waste problems but none have been entirely satisfactory. One proposal subjects solid wastes to dry distillation or pyrolysis at temperatures between about 900° C. and about 1000° C. without the injection of steam or oxygen and thereby attempts to produce crude oil. Scrubbing the gas products of this process is required and the scrubbing treatment causes pollution of water and the atmosphere.

Another proposal includes the steps of applying heat externally to a retort in which garbage is heated without internal combustion. The garbage is distilled or pyrolized at a temperature of about 400° C. The resulting gas is cracked, enriched, and scrubbed to make it suitable for heating and illuminating purposes. However, the scrubbing of the gas creates pollution problems and about 30% of the carbon remains unused and is discarded with the ash.

Another proposal calls for garbage to be destructively distilled while on a traveling grate in an open system. Organic material is thermally decomposed at temperatures between about 1000° F. and about 2000° F. in the absence of oxygen. Some 34–36% of the starting material remains at the completion of the process. Most of the gas produced during the process is consumed in the process and the gas which is not so consumed is heavily diluted with carbon dioxide and nitrogen and is not suitable for use in the chemical industry or release to the atmosphere.

As the public concern about air pollution has increased, stack heights have been increased to affect better dispersion of pollutants. Increasing stack heights add to the cost of constructing and maintaining stacks, yet provides no solution to the underlying problem, i.e., avoiding emission in the first instance of harmful substances such as sulfur oxides, chlorine gases, phosphor oxides, etc.

A significant factor in air pollution is the increasing level of gaseous airborne pollutants which combine with moisture in the air to produce acids, e.g., carbon dioxide, sulfur dioxide, and compounds of chlorine and fluorine. The carbon dioxide content in some industrial districts is as high as ten times normal. Acid forming pollutants have been found in some instances to increase the acidity of rainwater from its normal pH of about 6.9 to values of 4.0. Rainwater having a pH of 5.5 or lower will destroy aquatic life and can do substantial harm to buildings, monuments, and other structures.

One proposal for removing acid forming components from exhaust gases is to scrub the entire flow of exhaust gases with water and caustic prior to discharging them through a stack. However, scrubbing the entire exhaust gas flow requires large quantities of water, which are not always available, and requires costly, large capacity scrubbing equipment. Indeed, scrubbing the entire flow of exhaust gases from some incinerators requires at least half the amount of water, by weight, of the solid wastes burned in the incinerator. Treating the large volume of scrub water needed in such a process is very costly and contributes to the impracticality of scrubbing as a total solution to the acid pollutant problem.

The problem of disposing of exhaust gases is now recognized as a major concern in industrial countries throughout the world. Dispersing emissions through the use of tall stacks is no longer regarded as an acceptable solution. Applicant's U.S. Pat. No. 3,970,524 discloses a system for gasification of solid waste materials and a method for treating the resulting gases to produce commercially usable gases in such a manner that dispersion through stacks is not necessary. Solid waste materials are initially converted into combustion gas by partial oxidation in a combustion zone with a minimum amount of oxygen and subsequently purified into various components or fractions useful in industry. Purification occurs in stages by successive condensing steps whereby contaminants and undesired components are removed and desirable components are separated into useful gaseous fractions for heating boilers, firing gas turbines, providing district heat, and synthesis of ammonia and other chemical products, including plastics, dye stuffs and pharmaceuticals. One feature of the process is the use of a multichamber gas treatment unit in which noxious gas components are condensed, sublimed or "frozen out" and thereby separated from the clean usable gas components. However, the process discharges $CO_2$ to the atmosphere and, due to the high nitrogen content in the combustion gas, is not suitable for producing a synthesis gas which can be converted to a liquid fuel, such as methanol.

SUMMARY OF THE INVENTION

It is, therefore, an object of the present invention to overcome the environmental and economic drawbacks of the prior art and to provide a unique, improved process for the efficient treatment and conversion of solid waste to a synthesis gas suitable for making liquid fuel.

It is another object of the present invention to provide a process for the efficient treatment and conversion of solid waste which is capable of digesting all organic feed and for generating a combustion gas suitable for synthesis to liquid fuel.

It is still another object of the invention to provide a process for the efficient treatment and conversion of solid waste which is environmentally safe by virtue of substantially eliminating nitrogen from the combustion gas and, thereby, from the gases discharged to the atmosphere and by minimizing or eliminating the discharge of carbon dioxide.

It is yet another object of the invention to provide a process for the efficient treatment and conversion of solid waste to a synthesis gas suitable for making liquid fuel, such as methanol, which is highly efficient by virtue of converting a very high percentage of carbon in the solid waste to carbon monoxide, or at least to carbon dioxide, which compounds are both ultimately converted to methanol.

Other objects and advantages will become apparent from the following description and appended claims.

In accordance with the foregoing objects the present invention provides a process for the efficient treatment and conversion of solid waste to a synthesis gas suitable for making liquid fuel, such as methanol, whereby solid waste is converted into combustion gas in a continuously operating closed system by partial oxidation in a combustion zone with a sufficient amount of a mixture of high purity oxygen and carbon dioxide in the effective absence of nitrogen to affect a very high percentage conversion of carbon in the solid waste to carbon monoxide and carbon dioxide rather than to methane and higher hydrocarbons. The resulting products of combustion, including carbon dioxide, are separated into various components and reused in the process, converted to liquid fuel, such as methanol or discharged to the ambient as environmentally safe, pollution free gases.

Solid waste is burned in the presence of a mixture of high purity oxygen, at least 95% pure by volume, and carbon dioxide and the absence of auxiliary fuels, without the need for a catalyst, in a lower part or combustion zone of a reactor or retort. The gas flow required to carry the heat through the bed of the reactor is provided by recycling carbon dioxide produced during the process and using the carbon dioxide together with the high purity oxygen as the gaseous feed to the combustion process. This has the environmental benefit of utilizing, rather than discharging to the ambient, the carbon dioxide which is produced in the process. Most advantageously, the carbon dioxide is fed to the reactor in roughly equal proportions with the enriched oxygen, with a useful ratio of enriched oxygen to carbon dioxide being in the range 40:60 to 60:40, by volume.

Solid waste is burned in the presence of oxygen without the need for a catalyst in a lower part or combustion zone of a reactor or retort. Heat produced in the combustion process raises the temperature in the reactor to about 800°–1000° C. Gaseous combustion products rise through and intimately contact solid waste supported in a reduction zone above the combustion zone where some of the carbon dioxide is reduced to carbon monoxide. These gases pass into a carbonization zone above the reduction zone, where they volatilize and distill such fluids as moisture, tars and oils in and on the solid waste. Gases which rise from the carbonization zone are cooled by the incoming charge and are withdrawn from the retort. The unburned part of the solid waste is discharged from the combustion zone at the bottom of the retort. All but about 2% to 5% by volume of the solid waste is consumed in the process. The solid waste which remains for disposal is largely inert material which contains very little, not exceeding 1-2% by weight, wasted carbon.

Gases issuing from the retort are purified in stages by condensing and removing contaminants and undesired components. Tars and oils may be condensed in steps of progressively lowered temperatures. The tar and oil free gas is further purified by being cooled to below about −160° C. and separated into its condensable and non-condensable components. The condensable component may be "frozen out," i.e., converted into the liquid, solid, or sublimed phases. Such components are commonly referred to in the industry as a "subgas," a sublimable gas or a sublimation gas which when recovered may be recycled to a conventional $H_2$ make-up loop. The non-condensable components comprise a clean synthesis gas primarily comprising CO and $H_2$ which is suitable for use as the syn-gas feed, together with $CO_2$, in a conventional methanol synthesis loop.

The system of the present invention provides a relatively simple and economical method of recovering the most valuable components of solid waste and converting at least 50% of the solid waste to methanol. Implementation of a system for the practice of this method provides an eminently practical and environmentally desirable solution to the solid waste disposal problems suffered by communities in the United States and abroad. Not only does it utilize residential and industrial waste at no cost as the starting material, which represents a very large saving over other methanol production processes which use as the raw material methane or higher hydrocarbons or even coal, but the situation today permits a solid waste disposal facility to charge a fee for accepting the waste. Thus, the economics of converting solid waste to methanol according to the present invention justifies tolerating higher capital costs, if such should become necessary.

BRIEF DESCRIPTION OF THE DRAWINGS

A fuller understanding of the invention may be had by referring to the following description and claim taken in conjunction with the accompanying drawings in which:

DESCRIPTION OF THE PREFERRED EMBODIMENTS

A typical solid waste which may be utilized in the process of the present invention is municipal waste having approximately the composition shown in Table I.

TABLE I

| Components | Wt. % |
| --- | --- |
| Cellulosic Material | 60 |
| Plastic | 8 |
| Food waste | 6 |
| Yard waste | 6 |
| Wood | 7 |
| Other organic | 5 |
| Metals | 3 |
| Glass | 2 |
| Inerts | 3 |
| | 100 |

The elemental analysis of the typical waste of Table I, after removal of metals, glass and inerts, is shown in Table II.

TABLE II

| Component | Wt. % |
|---|---|
| Carbon | 47.1 |
| Hydrogen | 6.4 |
| Oxygen | 45.8 |
| Nitrogen | 0.6 |
| Sulfur | 0.1 |
| | 100.0 |

Solid waste such as this has a gross heating value of 18,000–19,000 KJ/Kg. As a consequence it could not be safely charged to conventional municipal incinerators since there would be a considerable risk of melting the gratings. Even with air injection cooling of the moving grates of incinerators using 75% excess air, insufficient of the generated heat would be dissipated. Moreover, conventional incinerators produce and expel ten times as much flue gas, by volume, as the present process for each unit weight of solid waste burned and, with any open system, such as is common for incinerators, the resulting air pollution is massive and, in many cases, in excess of environmental restrictions.

The composition of gas produced in the process of the present invention is influenced by several factors, primarily including (1) the reaction temperature in the combustion zone, (2) the composition of the solid waste and other materials introduced into the retort and the amount of such materials, and (3) the temperature, concentration and amounts of fluids introduced into the retort.

The principal materials introduced into the retort in addition to the solid waste are the oxidizing means for the partial oxidation of the solid waste (starved oxidation) comprising a blend of at least 95% by volume pure oxygen diluted with carbon dioxide, preferably in an oxygen to carbon dioxide ratio of 50:50 by volume but acceptably within the range 40:60 to 60:40. As a result of the aggressive scavenging action of highly enriched oxygen the process is able to digest the organic feed and achieve dissociation of all higher organic components with relatively short retention times in the retort. Moreover, by virtue of using high purity oxygen, nitrogen, an element which hampers methanol synthesis and is not easily separated from CO, is substantially excluded from the system. In accordance with the present invention, sufficient oxygen is introduced into the retort to optimize the conversion of organic components to CO, break down large organic molecules to compounds having not more than four carbon atoms and control the temperature in the retort to the range 800°–1000° C. Desirably, the amount of oxygen required, based upon pure oxygen, is 5% to 15% by weight of the solid waste charge, preferably 8% to 12% by weight, depending upon the composition of the charge and the reaction temperature. For example, inasmuch as the amount of oxygen required for combustion gas generation amounts to about 10% by weight of the solid waste charge based upon pure oxygen, nitrogen carried in with the oxygen is limited to less than about 0.5% by weight of the charge. Since the inherent nitrogen content of the waste material as charged is typically about 0.5% by weight of the charge, the present process contemplates that about 1% by weight nitrogen is admitted to the retort in the typical case.

The at least 95% pure oxygen required for the present process is readily available or can be made by well known techniques such as cryogenic techniques or vapor pressure swing adsorption (VPSA). The latter method is less costly and is preferred and the oxygen produced can be used not only for the solid waste gasification phase but also for hydrogen make-up by the partial oxidation method, as will be described more fully hereinafter.

Carbon dioxide is injected with the enriched oxygen into the reactor in order to provide the bulk gas flow necessary to carry the heat of combustion through the solid waste bed, to convert $CO_2$ to CO for use as a methanol building block (although, as will be seen, the present process also produces methanol from $CO_2$) and to assist in depressing the temperature in the reactor. At least these latter two purposes are achieved by virtue of the carbon dioxide taking part in the following endothermic reaction:

$$CO_2 + C \rightarrow 2CO$$

Inasmuch as the carbon dioxide injected into the reactor, as well as the carbon dioxide used in hydrogen make-up and methanol synthesis, is recycled from the carbon dioxide produced by the combustion of solid waste, an important characteristic of the present invention is that the produced carbon dioxide is used rather than discharged. This is environmentally significant since one of the greatest shortcomings of prior solid waste incineration processes is that they pollute the ambient air with carbon dioxide and, thus, contribute to the environmentally harmful acid rain and green-house effects.

In addition to the oxidizing means, steam may be introduced into the retort as a heat absorber to reduce the temperature therewithin. Tars and oils, recovered at a rate of about 2–3% by weight of the solid waste charge from the combustion gas during the process are advantageously recycled to the reactor to maintain a carburetting effect. No auxiliary fuel is needed for burning in the retort in view of the aggressive action of the high purity oxygen.

The injected streams of oxygen and carbon dioxide are preheated by penetrating the bed of ash in the lower part of the retort. Recycled tars and oils are also burned in the lower part of the retort. The highest temperature in the retort is above the bed of ash on the gratings on which the solid waste rests. As the waste in that zone is burned by the high purity oxygen-supported combustion, the resulting combustion gases are heated and, with the preheated oxygen and carbon dioxide, move upwardly through and in intimate contact with the solid waste. The waste above the gratings is directly heated by these rising combustion gases, carbon dioxide and oxygen, consuming the oxygen and breaking down the organic matter into compounds containing four carbons and less. The combustion gases are cooled as they give up heat to the solid waste and when they issue from the upper part of the retort they may be 600°–800° C. lower in temperature than the temperature in the combustion zone. For example, where the temperature in the combustion zone is about 900° C., the temperature of the gases discharging from the retort will be about 200°–300° C. or less. An autothermic gas generator such as the retort utilized herein allows a high thermal efficiency of about 80%±5% since the generated heat stays within the reactor and is transferred in direct heat exchange to the material sliding downwardly which has been dried and carbonized by the rising gases.

When solid waste is treated in the retort by burning in the presence of about 10% by weight oxygen based upon pure oxygen and an approximately equal amount of carbon dioxide and the temperature in the combustion zone is about 900° C., a typical gas stream leaving the retort will have a general composition which may be about as shown in Table III.

TABLE III

| Component | Vol. % | Wt. % |
| --- | --- | --- |
| Hydrogen | 31.1 | 2.8 |
| Carbon monoxide | 37.1 | 46.8 |
| Carbon dioxide | 17.3 | 34.1 |
| Methane | 6.8 | 4.9 |
| Ethane | 1.18 | 1.6 |
| Ethylene | 3.42 | 4.3 |
| Propane | 0.24 | 0.5 |
| Propylene | 1.75 | 3.3 |
| Butane | 0.19 | 0.5 |
| Oxygen | 0.07 | 0.1 |
| Nitrogen | 0.85 | 1.1 |

The desired temperature for the production of a gas of predetermined composition may be maintained by varying the amounts of oxygen, carbon dioxide and steam if used, which are introduced into the retort. In general the temperature will increase with the amount of oxygen which is introduced into the retort. Steam as well as carbon dioxide will exert a lowering effect on the temperature. Also, the higher the temperature of the preheated materials which are introduced into the retort, the higher will be the temperature in the retort.

It is known that high reaction temperatures, for example about 1200°-1300° C., favor an increased yield of hydrogen at the expense of carbon monoxide. Therefore, in accordance with the present invention, the operating temperature within the reactor is maintained within the range of 900°-1000° C. to encourage a high yield of carbon monoxide. This is because the carbon monoxide is an important source component for the subsequent conversions to methanol. If the conversion to methanol is to be highly efficient, the process cannot afford to lose the carbon that would be used up by operating the reactor in the 1200°-1300° C. range. As a result, the demand for hydrogen is met in other ways, for example by providing a hydrogen make-up system as will be described more fully hereinafter. In addition, maintenance of the lower operating temperature does not require a high combustion rate, which is consistent with the need in the present process to recycle $CO_2$ to the reactor and the effect of $CO_2$ in depressing the reactor temperature. Moreover, there are restrictions on $NO_x$ discharge to the atmosphere and the best way to avoid formation of nitrogen oxide (NO) is to maintain lower operating temperatures in the reactor.

With reference to Table III, it is noteworthy that almost 70% by volume of the combustion gas consists of hydrogen and carbon monoxide. At the conditions prevailing in the reactor enriched oxygen (at least 95% pure) is very aggressive and acts like a shredder, breaking down all components into units having no more than 4 carbon atoms and forming components such as CO, $H_2$, $CH_4$, $CO_2$ and some higher hydrocarbons. In the process virtually all of the oxygen is used up, with only about 0.1-0.2% by weight remaining in the gases which leave the retort.

Figure 1:
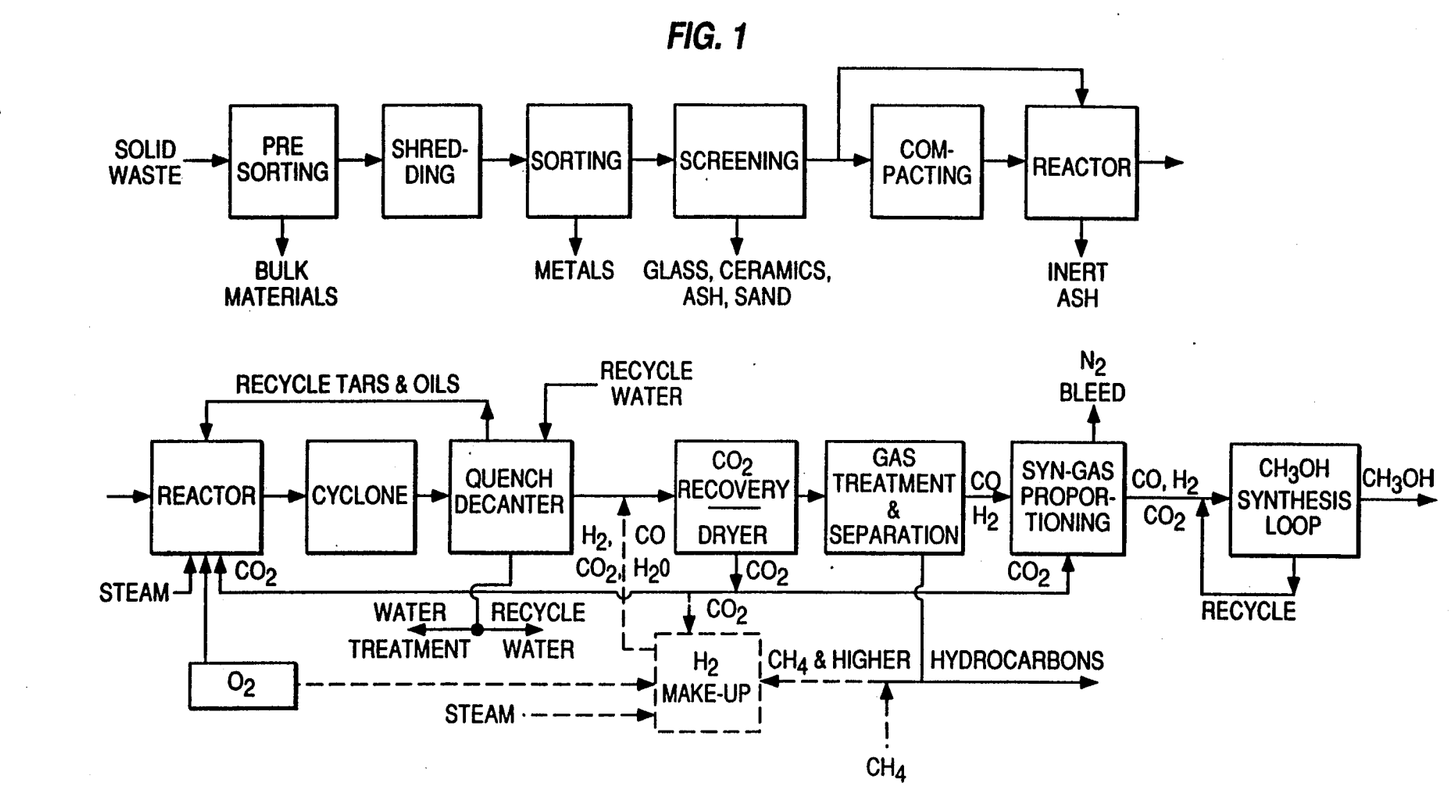
FIG. 1 is a block flow sheet of a system for practicing the present invention.
Figure 2:
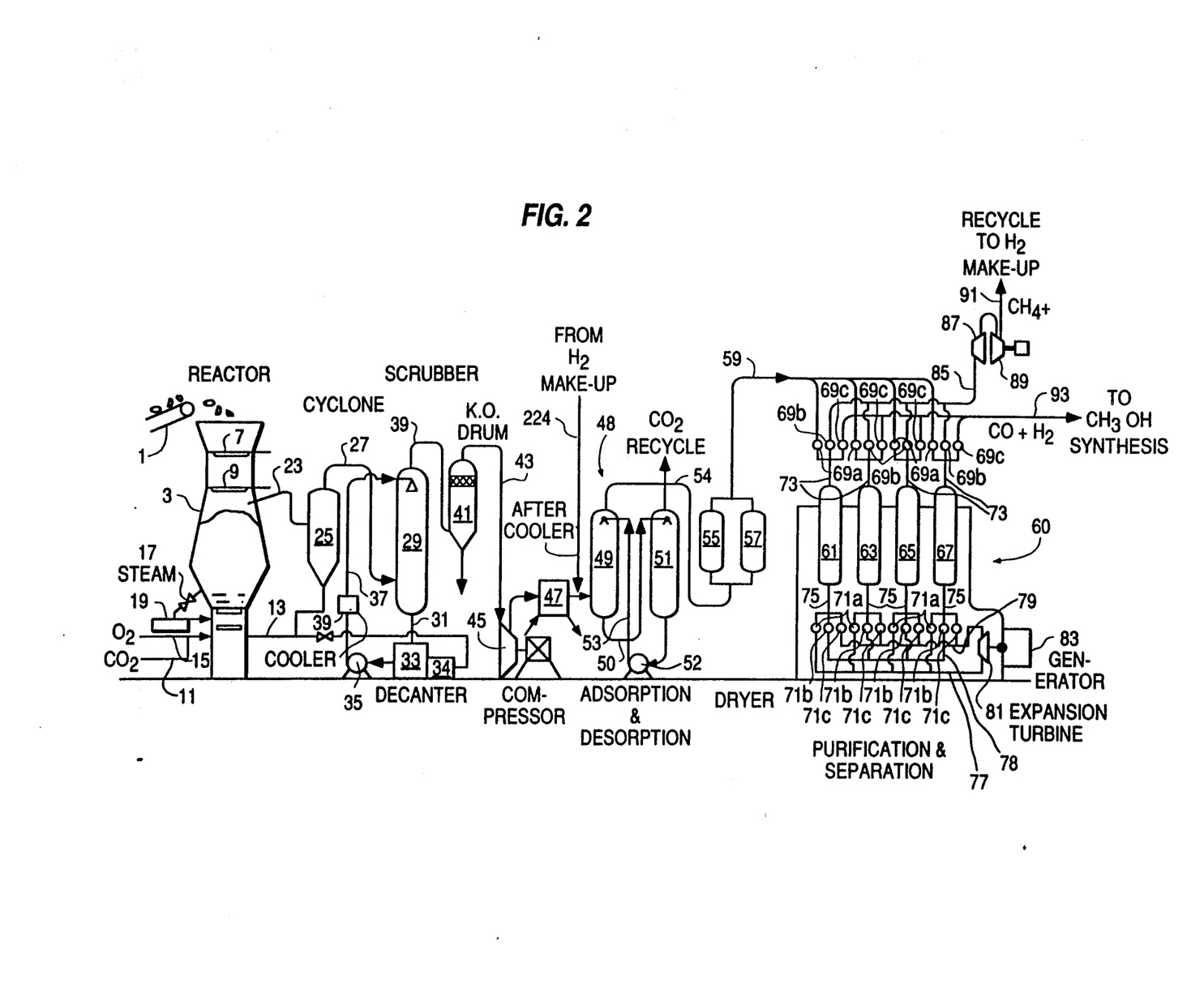
FIG. 2 is a schematic flow diagram of a system, including exemplary apparatus for practicing the FIG. 1 embodiment of the present invention.

Referring to FIGS. 1 and 2, the preferred process of the present invention and an apparatus for its practice are shown in block flow sheet and schematic flow diagram format. Solid waste to be treated by the present process typically contains glass, ferrous, and non-ferrous objects of varying size and configuration. As a first stage in the process these articles are removed in a series of steps indicated as pre-sorting, shredding, sorting, and screening in FIG. 1, but which can occur in any convenient sequence. During these steps the bulkier objects of glass and metal are removed mechanically or by hand, the remaining solid waste is shredded, ferrous materials are magnetically removed, the shredded solid waste is screened, e.g., using a series of shaker screens, to remove glass, ceramics, ash, sand, and the like, after which at least a portion of the waste is carried via conveyer to a conventional compacting station, such as a briquetting machine. The solid waste, at least partially in the form of compact briquettes, is placed upon conveyer 1 which transports the waste to a location atop retort 3.

Upper and lower doors 7, 9 permit solid waste to be introduced into retort 3 while preventing egress or escape of gas from within the retort. When a charge of solid waste is to be introduced into the retort, the upper door 7 is opened while the lower door 9 remains closed. When the charge on door 9 substantially fills the space between the two doors, the upper door 7 is closed and the lower door 9 is opened permitting the charge of solid waste to drop into the retort. Since pressure existing in the retort is slightly below ambient, i.e., in the range 4-6 inches of water below atmospheric regardless of the temperature, the doors 7, 9 are adequate to prevent the escape of gas during charging of the retort.

After the retort has been charged, as described, substantially pure oxygen and $CO_2$ are introduced into the lower part of the retort. In a preferred form of the invention retort 3 is a closed vertical furnace equipped with a rotating grating at its lower end for supporting the charge of solid waste thereon. Due to the aggressive scavenging action of high purity oxygen no auxiliary fuel need be burned in the retort although a continuous carburetting action is advantageously maintained by recycling, through line 13, tars and oils separated from the combustion gas. The burning of tars and oils takes place in what may be termed a "combustion zone" in the lower part of the retort. Carbon dioxide is introduced at 11 and admixed with enriched oxygen which is introduced at 15 into the lower part of the retort. Steam, when used, may be introduced at 17.

Oxygen and carbon dioxide are preheated in the lower part of the retort by the hot ash which has accumulated in a bed on the gratings supporting the solid waste. This hot ash, in addition, protects the gratings from overheating; utilizes the carbon carried with the ash, thereby minimizing unreacted carbon; and, drops only inerts for removal. The preheated oxygen and carbon dioxide initially heat the solid waste on the gratings. As the products of combustion rise in the retort, they intimately contact and heat the remaining solid waste with resultant vaporization and distillation of parts of the charge. Gases are withdrawn from the upper part of the retort, and treated, as will presently be described.

Although the charging of the solid waste into the retort is batchwise, the withdrawal of the produced gas is continuous. That gas is withdrawn from the retort through line 23 and is carried to particle separation unit 25 which is preferably a cyclone separator for separation of particulate matter as small as 50 microns in size from the gas. Separator 25 is preferably insulated to avoid heat loss.

Combustion gas which has been cleaned of particulate matter is ducted through conduit 27 into quench chamber 29 wherein it is cooled to about 50° C., as by being sprayed with water which has been removed from the combustion gases (which comprise about 20% by weight water) by condensation in chamber 29 and, thereafter, recycled to chamber 29. Inasmuch as there may be too much water in the waste to recycle all that condenses, any excess water is directed to a water treatment unit. The spray causes condensation of tars, oils and water from the combustion gas and dissolution of undesirable elements. As a result, a water phase and an organic condensate phase collect in first decanter section 33 via line 31. The lighter organic phase overflows from the top of the water phase into second decanter section 34 from which it is recycled via line 13 to retort 3 to provide a desired carburetting effect in the lower portion of the retort. The water phase remaining in first decanter section 33 is withdrawn and delivered by pump 35 through line 37, which includes a cooler 39, to the sprayhead in the upper portion of chamber 29.

Uncondensed gas from quench chamber 29 is directed via line 39 to knock-out drum 41 where any remaining moisture in the gas is removed on a demister pad. The remaining uncondensed gas is drawn from knock-out drum 41 through line 43 by gas compressor 45. Preferably, the gas is compressed to a pressure high enough that when the gas is subsequently isentropically expanded to about ambient pressure in turbine 81, as will be more fully described hereinafter, the gas will experience a temperature drop of at least 10° C. In a preferred embodiment, the gas is compressed to a pressure of about 50 psig and is reduced to a temperature of ambient or slightly above ambient, i.e., about 25°-35° C., by passing through after cooler 47. The gas from cooler 47 is directed into the $CO_2$ recovery unit 48 where $CO_2$ in the gas is separated from the other components to permit its recycle to retort 3 via line 11 for blending with the substantially pure oxygen introduced via line 15. In addition, as can be seen from FIG. 1, the carbon dioxide separated in unit 48 may be recycled to the hydrogen make-up unit to participate in the hydrogen production reactions and to the syn-gas proportioning unit to assure a desired carbon dioxide level in the methanol synthesis loop. Carbon dioxide recovery may be carried out by any one of many well-known recovery techniques including cryogenic methods such as the Rectisol Process, utilization of membranes or molecular sieves, adsorption and desorption and water-wash systems. The latter is probably the simplest and least expensive. However, it requires a pressure of at least 150 psi to produce about 90% efficiency of recovery and that yield of carbon dioxide may not be adequate in certain cases. Accordingly, adsorption/desorption recovery of $CO_2$ appears to be the preferred method as illustrated in FIG. 2 wherein the cooled and compressed gas stream exiting after cooler 47, including make-up hydrogen added thereto via hydrogen make-up line 224, is passed into conventional adsorption/desorption column 49 wherein it is contacted with a spray of adsorbent liquid for separating the $CO_2$ from the gas stream and carrying it from column 49 into adsorption/desorption column 51 via line 50. The $CO_2$-containing adsorbent releases $CO_2$ in column 51 and the separated $CO_2$ exiting from the top of column 51 is recycled throughout the system as illustrated in FIG. 1. The $CO_2$-free adsorbent is recycled to column 49 via pump 52 and return line 53. The substantially $CO_2$-free combustion gas exits from the top of column 49 via line 54 and passes into conventional drying columns 55, 57, e.g., containing an adsorbent such as silica gel, which are alternately placed on-line and regenerated, as necessary.

The gas from drying columns 55, 57 is directed via feed line 59 to cryogenic gas purification and separation unit 60 which is a secondary purification step to ensure that the gas is clean enough to be admitted to the methanol synthesis loop. Such a treatment is necessary due to the stringent specifications for syn-loop feed gas notwithstanding the close control of feed components to substantially exclude nitrogen and the incorporation of a scrubbing system 29 for removing tars and oils as well as noxious gases. Moreover, inasmuch as the gas charged to the purification system 60 is practically free of carbon dioxide, it can readily be separated into two fractions without need for a fractionating column. Specifically, the cryogenic purification system 60 separates the feed gas into a heavier fraction comprising components such as methane and higher hydrocarbons and a clean, lighter fraction consisting of hydrogen and carbon monoxide. The lighter fraction is charged to the methanol synthesis loop after it has been blended with carbon dioxide, hydrogen and methanol synthesis loop recycle gas and properly proportioned for the synthesis of methanol. The heavier fraction is desirably directed to a hydrogen make-up system where it is converted to hydrogen for use in the process of the present invention.

The cryogenic gas treatment and separation unit 60 is operable to separate the gases into condensable and non-condensable components by subliming or "freezing out" condensable components of relatively low volatility, e.g., $CH_4$ and components having up to four carbon atoms. The unit 60 includes four similar packed towers or columns 61, 63, 65, 67. Each of the towers 61, 63, 65, 67 is similar to a regenerator described by Russell B. Scott at pages 29-31 of *Cryogenic Engineering*, published in 1959 by D. Van Nostrand Co., Princeton, N.J. Towers 61, 63, 65, 67 contain loose solids, for example, ceramic balls, quartzite pebbles, steel shot, pancakes wound from thin corrugated aluminum ribbon, or other solids having relatively large surface area to volume ratios, relatively high heat capacitances and the capability of storing heat and resisting corrosion. Typically, the packing for the regenerator towers has a surface area to volume ratio and packing capability sufficient that the regenerator has a surface of 1000 to 2000 square ft. per cubic foot.

Automatic switch valves 69a, 69b, 69c and 71a, 71b, 71c are provided at opposite ends of the towers 61, 64, 65, 67 to control the flow of fluids into and out of the towers. Tower connection conduits 73, 75 communicate the ends of towers 61, 63, 65, 67 with the valves 69a, 69b, 69c and 71a, 71b, 71c, respectively.

A pair of transfer conduits 77, 79 connect with the valves 71a, 71c for passing gas to and through cooling means, which could be a heat exchanger, but, if gas pressure is high enough is preferably an expansion turbine 81. An expansion turbine has the advantage that it cools the gas more efficiently by substantially isentropic expansion while at the same time it produces useful shaft work. To convert the shaft work to a more useful form of energy, a power generator 83 is coupled to the drive shaft of the turbine 81. Following separation of the feed gas into heavier and lighter fractions, the heavier fraction is drawn from the system via acid gas conduit 85 by vacuum pump 87 after which it is compressed in compressor 89 and directed through discharge conduit 91 to the hydrogen make-up system. The lighter fraction is directed via syn-gas discharge conduit 93 to the syn-gas proportioning unit.

The manner by which gases are treated in the unit 60 may be visualized as that of subjecting the gases to four like cycles repeated time after time as long as exhaust gases are being produced by the system. During each of the four cycles, a different step is conducted simultaneously in each of the towers 61, 63, 65, 67. While one of the towers is being cooled by a flow of cooled purified gas, separation is taking place in another tower, and condensed or sublimed components are being removed from the remaining towers.

A first step of a first cycle is carried out by opening the valves 69a, 71a at each end of tower 61 and valves 69c, 71c at each end of tower 67. Gases will then flow through tower 61, will drive the turbine 81, and will flow through the tower 67. The gases expand in the turbine 81 and, as the gases expand, they are cooled. It is the flow of these cooled gases through the tower 67 that readies the tower 67 for a subsequent gas separation step. (It is assumed here that the tower 61 has already been pre-cooled in this manner in a previous cycle so that less volatile gas components loaded into the tower 61 will be sublimed or "frozen out".) The gases are allowed to flow in this manner for a short period of time, for example, for about 6 to 8 minutes. Energy extracted from the gases by the turbine 81 may be used to drive the generator 83.

Gas cools in pre-cooled tower 61 due to contact with the large surface area of the cooler solids in the tower. Less volatile components of the gas are condensed or converted into the solid phase and remain in tower 61. The more volatile, non-condensed and clean components of the gas pass out of tower 61 and, via turbine 81, through tower 67. This clean gas is purified in the sense that it has been freed from the "frozen out", sublimed or condensed components. The turbine 81 expands the gas, thus further cooling it, and delivers the gas at a pressure of typically about 5 psig into tower 67. The pressure at which the gases enter the tower 67 is not critical. What is required is that the pressure ratio reduction effected in the turbine 81 is of sufficient magnitude to adequately cool the gases so the gases can properly chill the tower 67. The clean gas exiting tower 67, consisting of methanol synthesis gas components hydrogen and carbon monoxide, is directed via syn-gas discharge conduit 93 to the syn-gas proportioning unit.

A second step of the first cycle (which is carried out simultaneously with the loading of exhaust gas into the tower 61 and the cooling of the tower 67) is that of cleaning previously loaded towers by revaporizing the "frozen out" sublimed or condensed components remaining in those towers from prior cycles. This step is carried out, for example in connection with towers 63 and 65, by closing the valves 69a, 69b and 69c at the upper end of tower 63 and by connecting the upper end of tower 65 through valve 69b to the vacuum pump 87 and compressor 89. The respective lower ends of towers 63 and 65 are connected together in series via connect conduit 78 by opening valves 71b at the lower end of each of towers 63, 65 so that the pump 87 operates to reduce the pressure in the towers 63, 65 by a ratio of about 10 to 1. As pressure in the towers is reduced, the "frozen out," sublimed or condensed components are revaporized to form a hydrocarbon gas which is drawn out of the towers 63, 65. The hydrocarbon gas typically consists mainly of $CH_4$ with small amounts of up to $C_4$ hydrocarbons. The withdrawn hydrocarbon gas is compressed by the compressor 89 and is discharged into the hydrocarbon gas discharge conduit 91 which desirably directs it to the $H_2$ make-up system, as will be more fully described hereinafter.

The second cycle is like the one just described and consists of a first step of passing gases from the conduit 59 through one of the valves 69a into the cooled tower 67, separating, by "freezing out" or subliming, components of the gases in that tower, cooling the separated clean gas leaving tower 67 in the turbine 81 and passing the cooled, expanded clean gas through the recently cleaned tower 63 to chill that tower in preparation for receiving the next charge of exhaust gases from conduit 59. A second step is that of simultaneously revaporizing the "frozen out", sublimed or condensed components which remain in the towers 65, 61 from the prior cycle to clean these towers in preparation for chilling during the next cycle.

The third cycle is like the two foregoing cycles. Its first step is that of passing gases from the conduit 59 into the tower 63 to separate out gaseous components and cooling the just cleaned tower 65 with the separated clean gas fraction from tower 63 and turbine cooling means 81. A second step is to clean towers 61, 67 by revaporizing components remaining in the towers 61, 67 from previous cycles by withdrawing them through vacuum pump 81 and compressor 89.

The fourth cycle is like the three foregoing cycles. Its first step is that of passing gases from the conduit 59 into the tower 65 to separate out gaseous components and cooling the just cleaned tower 61 with the separated clean gas fraction from tower 65 and turbine cooling means 81. A second step is to clean towers 67, 63 by revaporizing components remaining in the towers 67, 63 from previous cycles by withdrawing them through vacuum pump 87 and compressor 89.

Typically, in a municipal waste system, the gasification occurring in retort 3 produces about one-third of the hydrogen which is ultimately needed in the methanol synthesis reactions. Clearly, hydrogen could be purchased for use in the synthesis and frequently that is the preferred course of action. Alternatively, make-up hydrogen can be made by any one of several well-known techniques including electrolytic methods, thermal dissociation of water, steam-methane reforming, partial oxidation of hydrocarbons and shift conversion of carbon monoxide. However, the heavier fraction separated by the cryogenic purification and separation system comprises methane and up to $C_4$ hydrocarbons which can readily be converted to hydrogen in an economical manner. Therefore, according to the present invention, if make-up hydrogen is not purchased it is preferred that this fraction be utilized, rather than discarded. In this connection, the gas stream containing methane and higher hydrocarbons is directed via hydrocarbon gas discharge line 91 to the $H_2$ make-up system wherein the methane and higher hydrocarbons in the stream are converted by either reforming conversion in the presence of carbon dioxide or partial oxidation to CO and $H_2$ with further conversion of the reaction product CO by shift conversion to $H_2$. In this way the amount of hydrogen make-up can be controlled by controlling the amount of hydrocarbon gas reaching the hydrogen make-up system via discharge conduit 91. Additional methane may optionally be added to the system via conduit 91 should there be insufficient hydrocarbons in the hydrocarbon gas discharge to meet the hydrogen demands of the methanol synthesis loop.

One of the following two reactions take place in the hydrogen make-up system.

Reforming $$3 CH_4 + CO_2 + 2H_2O \longrightarrow 4CO + 8H_2$$

or

Partial Oxidation $$CH_4 + \tfrac{1}{2}O_2 \longrightarrow CO + 2H_2$$

The partial oxidation reaction appears advantageous, particularly at start-up, since the present process may have insufficient carbon dioxide available at that time but has substantially pure oxygen available for injecting into retort 3. In addition, the reaction is exothermic ($-8.53$ kcal) and rapid and energy can be saved by generating heat within the system. Moreover, the reaction can readily utilize as reactants the $CH_4$ and higher hydrocarbons exiting the cryogenic purification and separation system 60 as the heavy fraction. On the other hand, the $CO_2$ reforming reaction advantageously utilizes the carbon dioxide produced in the present process and minimizes any need to discharge it to the atmosphere. In either case, however, whether partial oxidation or reforming is practiced, it has been found that the hydrogen generated is insufficient to meet the needs of the methanol synthesis loop. Therefore, it is desirable to utilize the reaction product CO by charging it to a shift reactor where it undergoes the following catalytic shift conversion reaction at temperatures of about 800° C.

$$CO + H_2O \rightarrow CO_2 + H_2$$

Figure 4:
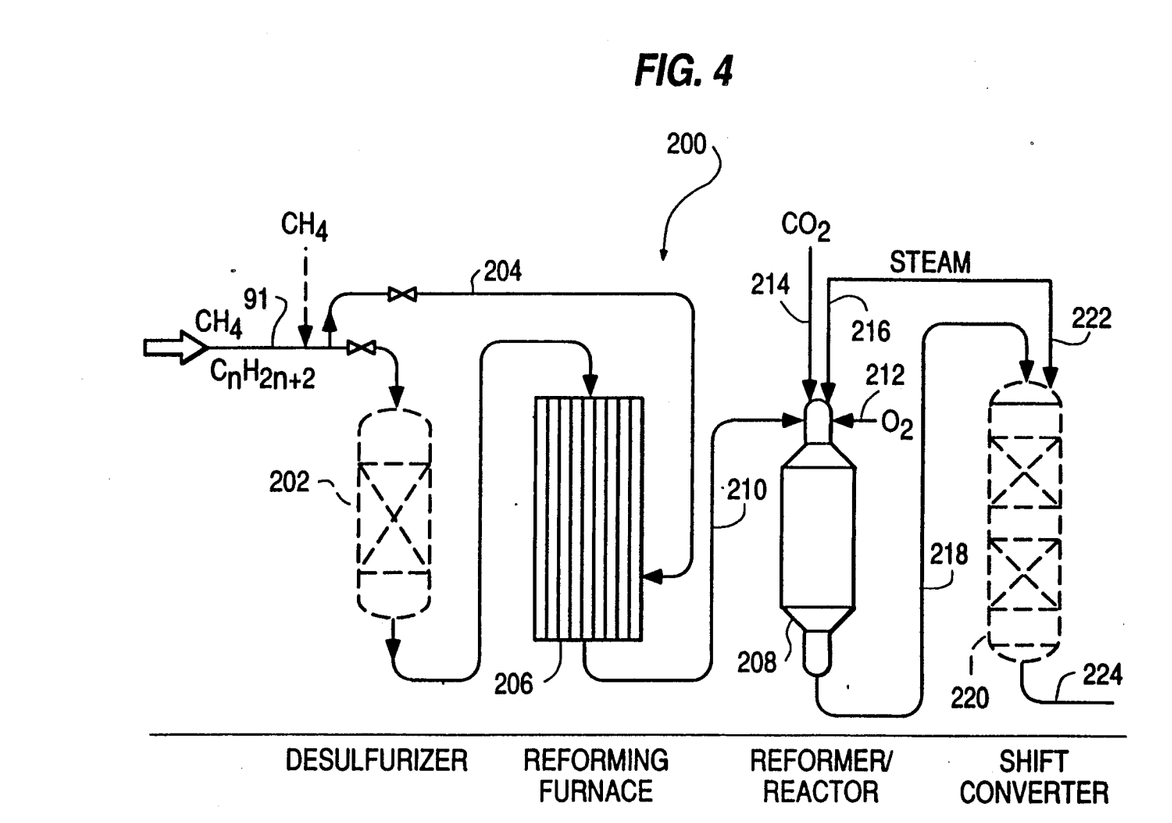
FIG. 4 is a schematic flow diagram of an illustrative hydrogen make-up system for use in the FIG. 1 embodiment of the present invention.

Referring to FIG. 4 there is shown a hydrogen make-up system 200 which is desirable for use in connection with the present process. Hydrocarbon gas discharge conduit 91 delivers a gas comprising methane and higher hydrocarbons (up to $C_4$) to system 200 wherein it is first passed through desulfurizing unit 202 in which any sulfur in the solid waste feed which has escaped removal in the scrubbing or gas purification system may be removed by conventional techniques, e.g., using activated carbon. Should the sulfur content of the entering gas stream be sufficiently minimal that desulfurization is not necessary, desulfurizing unit 202 may be bypassed via conduit 204 and the gas delivered directly to reforming furnace 206. The sulfur-free predominantly methane gas is heated from ambient up to about 800° C. in reforming furnace 206 to prepare it for the high temperature favored hydrogen production reactions which occur in reformer/reactor 208. Feed to the reformer/reactor 208 comprises the heated, sulfur-free predominantly methane stream entering via line 210 and either carbon dioxide or oxygen depending upon whether the entering stream is to be reformed in the presence of carbon dioxide or partially oxidized. Generally, if the feed stream is relatively heavy in the higher hydrocarbons, partial oxidation is the process of choice and oxygen is fed to reformer/reactor 208 via line 212. If the feed stream is relatively heavy in $CH_4$ content, then reforming is the process of choice and carbon dioxide and steam are fed to reformer/reactor 208 via lines 214 and 216 respectively. The feeding of steam is optional during partial oxidation. The reforming or partial oxidation reactions occur in the presence of well known catalysts under well known reaction conditions to produce an exit stream of carbon monoxide and hydrogen. Typically, as will be understood more fully from the illustrative example set forth hereinafter, the quantity of hydrogen produced is less than the amount needed in the methanol synthesis loop. One alternative, which is preferred, for producing more hydrogen is to feed the high temperature stream exiting reformer/reactor 208 via conduit 218 to shift converter 220 in which the well known shift conversion reaction with steam injected via line 222 occurs to convert the carbon monoxide to additional hydrogen and carbon dioxide. The hydrogen make-up stream 224 exiting shift converter 220 contains a major proportion of hydrogen, a minor proportion of carbon monoxide and small quantities of carbon dioxide and water. The stream is injected into the present process to provide needed hydrogen make-up at a point upstream of the carbon dioxide recovery units. Desirably, the stream is cooled to about ambient temperature and injected immediately upstream of adsorption/desorption unit 49.

The lighter fraction separated by the cryogenic gas separation and purification system 60 consists of CO and $H_2$. This comprises a substantial portion of the feed gas to the methanol synthesis loop. The efficiency of the synthesis loop depends not only on the type of catalyst or operating pressure and temperature, parameters which are relatively easy to control, but also on the proper composition of the syn-gas fed to the loop. Thus, it is essential to keep nitrogen at a very minimal concentration in the gas stream to avoid having to remove the inert fraction by bleeding a stream of gas with nitrogen, resulting in unnecessary losses of other valuable compounds. In particular, the syn-gas must be adjusted to at least stoichiometric proportions of hydrogen, carbon monoxide and carbon dioxide, the reactants which are utilized in the loop to produce methanol in accordance with the present invention.

The reactions which occur in the methanol synthesis loop are the following:

$$CO + 2H_2 \rightarrow CH_3OH \ (-90.84 \ KJ/Kmol)$$

$$CO_2 + 3H_2 \rightarrow CH_3OH + H_2O \ (-49.57 \ KJ/Kmol)$$

Use of $CO_2$ in the synthesis loop has several previously unappreciated advantages. First, the exothermic reaction using $CO_2$ is not as vigorous as with CO, which makes it easier to control reaction conditions. Second, $CO_2$ is utilized for a productive purpose rather than merely being discarded. Third, any reduction in the amount of $CO_2$ released to the atmosphere is environmentally beneficial in decreasing the "greenhouse" effect.

The CO and $H_2$ comprising the pure gas discharge from the purification and separation system 60 are directed to the syn-gas proportioning unit (see FIG. 1) wherein the $CO:H_2$ concentration ratio may be monitored in order to determine the amount of $CO_2$ which must be diverted from the carbon dioxide recovery system 48 into admixture with the CO and $H_2$. It is generally most desirable to proportion the syn-loop feed gas in the proportioning unit to as close to a stoichiometric mixture as possible with a slight excess of hydrogen and about 12% by volume carbon dioxide.

Figure 3:
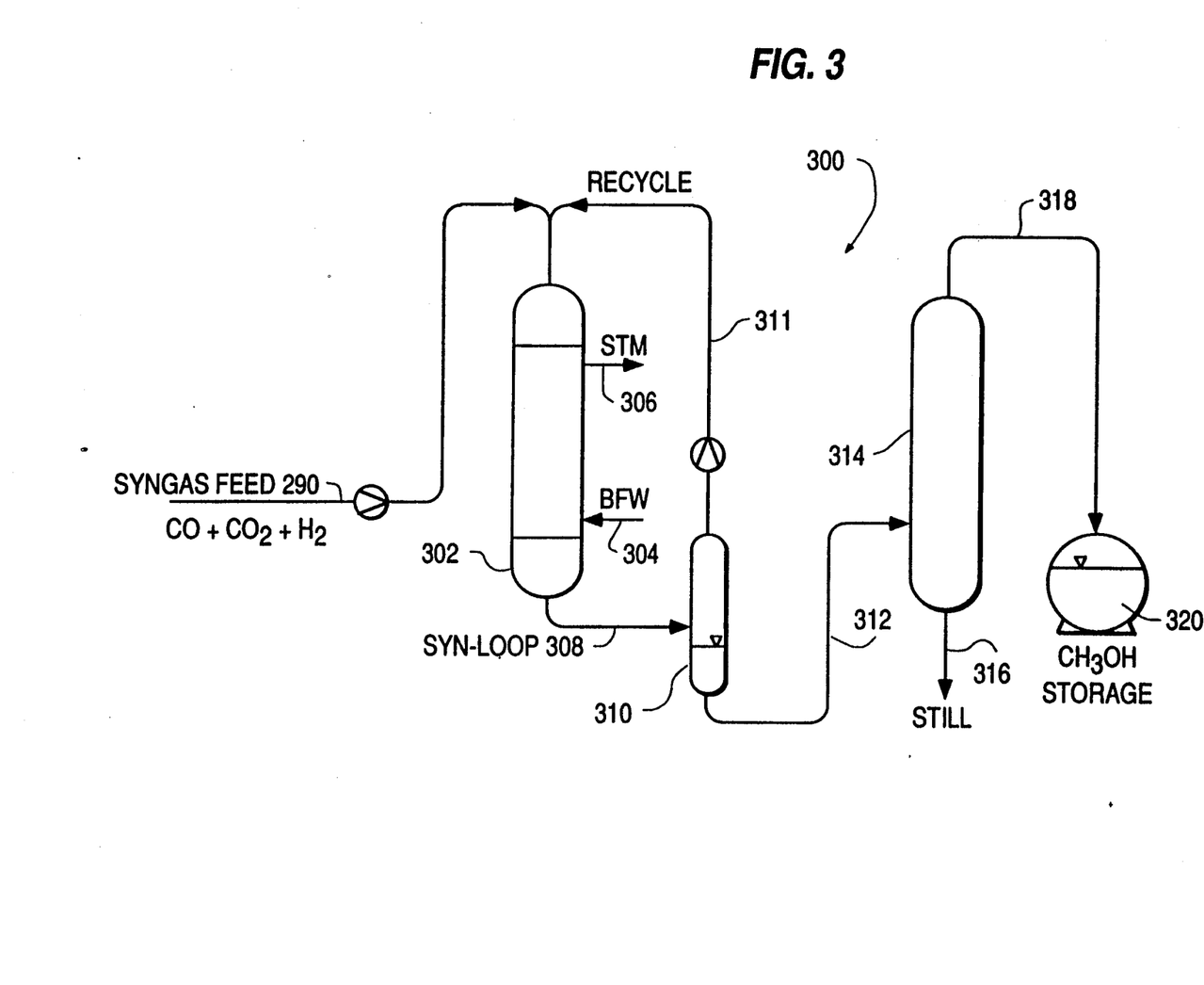
FIG. 3 is a schematic flow diagram of an illustrative methanol synthesis loop for use in the FIG. 1 embodiment of the present invention.

The syn-gas feed from the regenerators combined with CO$_2$ from the recovery unit is adjusted to the desired proportions, suitably compressed and heated by well-known methods and directed at a temperature and pressure of about 300° C. and 1400 psi from the proportioning unit via syn-gas feed conduit 290 to the methanol synthesis loop 300. The CO, CO$_2$ and H$_2$ exothermically react in the presence of a catalyst in syn-loop reactor 302 as is well known in the art. Excess heat generated during the reaction is cooled by boiler feed water inlet flow through line 304 and is removed as steam via line 306. The reactions yield an approximately 60% conversion per run through reactor 302. As a result, reaction product methanol and by-product higher alcohols together with unreacted CO, CO$_2$ and H$_2$ are directed from reactor 302 via product removal line 308 to separator 310 wherein the CO, CO$_2$ and H$_2$ gases are separated from the by-product alcohols and returned to reactor 302 via recycle conduit 311. The alcohols are carried via still feed line 312 to fractionating column 314 where the heavier alcohols are separated and removed from the bottom of the still through still discharge conduit 316 while substantially pure methanol is carried via methanol supply line 318 to storage 320.

The process of the present invention will be better understood and the high efficiency of solid waste conversion to methanol will be better appreciated from the following example which is intended to illustrate, but not to limit, the scope of the invention.

EXAMPLE

A feed of 5 tons/hour of the solid waste described in Tables I and II was gasified at about 900° C. in a retort into which a 50:50 by volume gas stream of 95% pure O$_2$ (comprising about 10% by weight of the solid waste discharge) and CO$_2$ was injected to produce a combustion gas leaving the retort having the composition shown in Table III. At this feed level, the gas contains about 135 kg/hr H$_2$, 2260 kg/hr CO and 1650 kg/hr CO$_2$.

According to the reaction:

$$CO + 2H_2 \rightarrow CH_3OH,$$

starting with 2260 kg/hr CO (80.7 Kmol/hr) yields 80.7 Kmol/hr or 2583 kg/hr CH$_3$OH. To achieve this requires 161.4 Kmol/hr or 323 kg/hr H$_2$.

According to the reaction:

$$CO_2 + 3H_2 \rightarrow CH_3OH + H_2O,$$

starting with 12% by volume of the syn-gas feed stream of CO$_2$ requires (0.12) (2583)=310 kg/hr CO$_2$ (7.05 Kmol/hr). This reactant concentration yields 7.05 Kmol/hr or 226 kg/hr CH$_3$OH. To achieve this requires 21.15 Kmol/hr or 42 kg/hr H$_2$.

The total H$_2$ required by the methanol synthesis reactions is 323+42=365 kg/hr. Since gasification of the solid waste produces only 135 kg/hr, there is a 230 kg/hr H$_2$ shortfall which the present process desirably supplies via H$_2$ make-up.

The total methanol produced by the methanol synthesis reactions is 2,583+226=2,809 kg/hr. Since the actual solid waste feed to the reactor is 5 tons/hr or 4,536 kg/hr, the efficiency of methanol conversion is:

$$\text{Theoretical Efficiency} = \frac{\text{methanol produced}}{\text{solid waste fed}}$$

$$\text{Theoretical Efficiency} = \frac{2809}{4536} = 61.9\%$$

Notwithstanding that the 61.9% efficiency of the present process is only theoretical, it demonstrates that in actual practice conversion efficiencies of 50% or greater are readily attainable.

INDUSTRIAL APPLICABILITY

In accordance with the present invention there has been provided a solid waste disposal and conversion method which is designed especially for production of a gas suitable for synthesis gas preparation and conversion to methanol. It is a true recycling process wherein all components of the solid waste feed are reused in an economical fashion and, most importantly, in an environmentally responsible manner. Pollution control is a foremost objective of the process and is rigorously observed throughout. Thus, the process is operated in a closed system with the gasification phase conducted at a slight negative pressure to avoid inadvertent discharge of components. Only inert ash or slag, glass, ceramics, and the like are discarded. Moreover, the system makes important use of the carbon dioxide produced by gasification in three separate operations: to dilute oxygen as feed to the retort; as a reactant in the hydrogen make-up system; and, as a feed component to the syn-loop for the synthesis of methanol. This is in sharp contrast to the typical incineration or gasification process which discharges carbon dioxide to the atmosphere as a pollutant and a major contributor to the "green-house effect." In addition, by virtue of breaking down all higher components of organic origin to basic compounds of not more than four carbon atoms, the release of noxious acid gas is avoided. Instead, the methane and up to C$_4$ hydrocarbons produced may advantageously be utilized in producing make-up hydrogen. Any tars and oils in the solid waste are recovered and recycled and, thus, contribute to higher thermal efficiency of the process.

This favorable environmental result is attainable together with the conversion of at least 50% of the solid waste to methanol in accordance with the present process. In large part this is attributable to the utilization of an autothermic reactor which utilizes the heat generated within the system to minimize the losses and direct heat exchange to optimize the process and to convert a high percentage of the carbon in the solid waste to CO and CO$_2$ with very little carbon in other compounds to permit the conversion of virtually all of the carbon in the solid waste to methanol. As a result, high thermal efficiencies of about 80% and high solid waste conversion to methanol in excess of 50% are achieved. It is also attributable to the utilization of regenerators at low pressures (about 50 psi) for separating the combustion gas into a lighter fraction consisting of carbon monoxide and hydrogen and a heavier fraction comprising methane and higher (but only up to C$_4$) hydrocarbons. It is in part attributable to the elimination of nitrogen by recycling carbon dioxide to dilute the highly pure feed oxygen and to provide the bulk gas flow necessary to operate a gasification system. Finally, it is largely attributable to the utilization, rather than discharge, of produced carbon dioxide in the gasification, hydrogen make-up and methanol synthesis processes.

While the invention has been described with reference to particular embodiments thereof it will be understood that numerous modifications may be made by those skilled in the art without actually departing from the scope of the invention. For example, the apparatus and methods referred to in the specification and illustrated in FIG. 2 may be replaced by other well known apparatus and methods for achieving the same purpose. In addition, while the term "solid waste" has been used herein for brevity of description, it will be appreciated that the term includes and comprehends the waste materials described herein, namely, municipal waste, as well as agricultural waste including manures and the like, industrial waste including plastic articles, rubber articles and contaminated petroleum fractions, waste vegetable matter, animal matter including hides, bones and the like, garbage and waste paper. Accordingly all modifications and equivalents may be resorted to which fall within the scope of the invention as claimed.

I claim:

1. A process for converting solid waste into a synthesis gas suitable for producing liquid fuel, which minimizes or eliminates adverse environmental effects resulting from the discharge of gaseous materials to the atmosphere, comprising the steps of:
   (a) partially oxidizing and combusting solid waste material in a closed combustion zone at a temperature in the range 800°–1000° C. and at a pressure below ambient by introducing into said combustion zone a gaseous oxidant comprising oxygen having a purity of at least 95% by volume and carbon dioxide, said oxidant having an oxygen to carbon dioxide ration, by volume, in the range 60:40 to 40:60 for producing combustion gases;
   (b) conducting said combustion gases, oxygen and carbon dioxide through and in intimate contact with said solid waste material;
   (c) withdrawing from said closed combustion zone a producer gas comprising said combustion gases and any unreacted oxygen and carbon dioxide;
   (d) removing particulate matter from said producer gas;
   (e) separating carbon dioxide from said producer gas and recycling at least a portion of said separated carbon dioxide to said combustion zone for providing the carbon dioxide introduced into said zone;
   (f) separating the less volatile, condensable components of said carbon dioxide-free producer gas, comprising methane and higher hydrocarbons, from the more volatile, non-condensable synthesis gas components thereof, comprising carbon monoxide and hydrogen; and
   (g) compressing said producer gas at some time prior to the commencement of step (e) wherein said less volatile components are separated from said more volatile components by cooling said carbon dioxide-free gases wherein said carbon dioxide gas is cooled by contacting said gas with relatively large surface area to volume ratio solids which are cooler than said gas, whereby said gas cools by transferring heat to said solids, said gas being sufficiently cooled by contact with said solids that the less volatile components of said gas condense or sublime on said solids.

2. A process, as claimed in claim 1, wherein said producer gas is cooled and tars and oils are removed therefrom prior to the compressing of said producer gas.

3. A process, as claimed in claim 2, wherein at least a portion of said tars and oils are introduced into the combustion zone.

4. A process, as claimed in claim 1, additionally including the step of injecting steam into the combustion zone.

5. A process, as claimed in claim 1, where a pressure of about 4 to 6 inches of water below atmospheric pressure is maintained in the combustion zone.

6. A process, as claimed in claim 1, wherein said producer gas is compressed to a high enough pressure that subsequent isentropic expansion thereof to about ambient pressure causes at least a 10° C. temperature drop in said gas.

7. A process, as claimed in claim 6, wherein said producer gas is compressed to a pressure of about 50 psig.

8. A process, as claimed in claim 1, wherein said producer gas is cooled to the range from about 25°–35° C. at some time prior to the commencement of step (e).

9. A process, as claimed in claim 1, wherein from 8 to 12% oxygen by weight of said solid waste material, based upon pure oxygen, is introduced into said combustion zone.

10. A process, as claimed in claim 9, wherein about 10% oxygen by weight of said solid waste material, based upon pure oxygen, is introduced into said combustion zone.

11. A process, as claimed in claim 1, wherein said carbon dioxide-free gas is further cooled by substantially isentropic expansion of said gas after said less volatile components are separated in step (f).

12. A process, as claimed in claim 1, including the step of compacting at least a portion of the solid waste into briquette-like solids prior to introduction into said combustion zone.

13. A process, as claimed in claim 1, wherein said oxygen to carbon dioxide ratio is about 50:50.

14. A process, as claimed in claim 1, wherein said solid waste is arranged vertically in said combustion zone for conducting said gases, oxygen and carbon dioxide up through and in intimate contact with said solid waste.

15. A process as claimed in claim 1, wherein said solid waste is arranged vertically in said combustion zone for conducting said gases, oxygen and carbon dioxide up through and in intimate contact with said solid waste; said producer gas is cooled and tars and oils are removed therefrom prior to the compressing of said producer gas; said pressure in the combustion zone is maintained in the range from about 4 to 6 inches of water below atmospheric; and said producer gas is cooled to about ambient temperature at some time prior to the commencement of step (e).

16. A process, as claimed in claim 15, including the steps of admixing said carbon monoxide, hydrogen and at least a portion of said separated carbon dioxide from step (e), adjusting said admixture to at least stoichiometric proportions and reacting the resulting admixed gas mixture to form methanol.

17. A process, as claimed in claim 16, wherein said solids define a packed tower through which compressed carbon dioxide-free gas is passed for separation into condensable and non-condensable components, and said condensed or sublimed, less volatile components being recovered by partially evacuating said tower for revaporizing said components.

18. A process, as claimed in claim 16, wherein said less volatile components are converted by chemical reaction to hydrogen.

19. A process, as claimed in claim 18, wherein said separated, less volatile components are reacted with steam and at least a portion of said separated carbon dioxide from step (e) to form carbon monoxide and hydrogen as reaction products.

20. A process, as claimed in claim 18, wherein said hydrogen is recycled into admixture with said producer gas at some time prior to the commencement of step (e).

21. A process, as claimed in claim 1, wherein said condensed or sublimed, less volatile components are recovered by revaporizing said components.

22. A process for converting solid waste into a synthesis gas suitable for producing liquid fuel, which minimizes or eliminates adverse environmental effects resulting from the discharge of gaseous materials to the atmosphere, comprising the steps of:

(a) partially oxidizing and combusting solid waste material in a closed combustion zone at a temperature in the range 800°–1000° C. and at a pressure below ambient by introducing into said combustion zone a gaseous oxidant comprising oxygen having a purity of at least 95% by volume and carbon dioxide, said oxidant having an oxygen to carbon dioxide ration, by volume, in the range 60:40 to 40:60 for producing combustion gases;

(b) conducting said combustion gases, oxygen and carbon dioxide through and in intimate contact with said solid waste material;

(c) withdrawing from said closed combustion zone a producer gas comprising said combustion gases and any unreacted oxygen and carbon dioxide;

(d) removing particulate matter from said producer gas;

(e) separating carbon dioxide from said producer gas and recycling at least a portion of said separated carbon dioxide to said combustion zone for providing the carbon dioxide introduced into said zone;

(f) separating the less volatile, condensable components of said carbon dioxide-free producer gas, comprising methane and higher hydrocarbons, from the more volatile, non-condensable synthesis gas components thereof, comprising carbon monoxide and hydrogen; and (g) compressing said producer gas at some time prior to the commencement of step (e) wherein said less volatile components are separated from said more volatile components by cooling said carbon dioxide-free gases wherein said carbon dioxide gas is cooled by contacting said gas with relatively large surface area to volume ratio solids which are cooler than said gas, whereby said gas cools by transferring heat to said solids, said solids defining a packed tower through which compressed carbon dioxide-free gas is passed for separation into condensable and non-condensable components, said gas is sufficiently cooled by contact with said solids that the less volatile components of said gas condense or sublime on said solids, and said condensed or sublimed, less volatile components are recovered by partially evacuating said tower for revaporizing said components.

23. A process, as claimed in claim 21 or 22, wherein at least a portion of said separated, less volatile components are converted by chemical reaction to hydrogen.

24. A process, as claimed in claim 23, wherein said portion of the separated, less volatile components are reacted with, steam and at least a portion of said carbon dioxide from step (e) to form carbon monoxide and hydrogen as reaction products.

25. A process, as claimed in claim 24, wherein said reaction product carbon monoxide is converted by further chemical reaction to hydrogen.

26. A process, as claimed in claim 25, wherein said hydrogen is recycled into admixture with said producer gas at some time prior to the commencement of step (e).

27. A process, as claimed in claim 24, including the step of admixing said more volatile components and at least a portion of said separated carbon dioxide from step (e) and reacting the resulting admixed gas mixture to form said liquid fuel.

28. A process, as claimed in claim 27, wherein said liquid fuel is methanol.

29. A process, as claimed in claim 28, wherein said carbon monoxide, hydrogen and carbon dioxide admixture is adjusted to at least stoichiometric proportions prior to reacting to form methanol.

30. A process, as claimed in claim 29, wherein said admixture comprises a slight excess above the stoichiometric proportion of hydrogen and about 12% by volume carbon dioxide.

31. A process, as claimed in claim 23, wherein said portion of the separated, less volatile components are reacted with substantially pure oxygen to form carbon monoxide and hydrogen as reaction products.

32. A process, as claimed in claim 31, wherein said reaction product carbon monoxide is converted by further chemical reaction to hydrogen.

33. A process, as claimed in claim 32, wherein said hydrogen is recycled into admixture with said producer gas at some time prior to the commencement of step (e).

34. A process, as claimed in claim 23, wherein said hydrogen is recycled into admixture with said producer gas at some time prior to the commencement of step (e).

35. A process, as claimed in claim 22, including the step of admixing said more volatile components and at least a portion of said separated carbon dioxide from step (e) and reacting the resulting admixed gas mixture to form said liquid fuel.

36. A process, as claimed in claim 35, wherein said liquid fuel is methanol.

37. A process, as claimed in claim 36, wherein said carbon monoxide, hydrogen and carbon dioxide admixture is adjusted to at least stoichiometric proportions prior to reacting to form methanol.

38. A process, as claimed in claim 37, wherein said admixture comprises a slight excess above the stoichiometric proportion of hydrogen and about 12% by volume carbon dioxide.

* * * * *